United States Patent [19]

Cue et al.

[11] Patent Number: 4,477,671
[45] Date of Patent: Oct. 16, 1984

[54] 3-ACETOXY OR BENZYLOXY-2-ACETOXYMETHYL-6-[1-ACETOXY-2-(N-TERT-BUTYLACETAMIDO)ETHYL]PYRIDINE INTERMEDIATES

[75] Inventors: Berkeley W. Cue, Gales Ferry; Stephen S. Massett, Groton, both of Conn.

[73] Assignee: Pfizer Inc., New York, N.Y.

[21] Appl. No.: 500,210

[22] Filed: Jun. 2, 1983

Related U.S. Application Data

[62] Division of Ser. No. 340,172, Jan. 18, 1982, , which is a division of Ser. No. 232,923, Feb. 9, 1981, abandoned.

[51] Int. Cl.$^3$ .......................................... C07D 213/75
[52] U.S. Cl. .................................. 546/291; 546/115; 546/300; 424/263
[58] Field of Search ........................................ 546/291

[56] References Cited

U.S. PATENT DOCUMENTS

| | | | |
|---|---|---|---|
| 3,786,160 | 1/1974 | Barth | 424/263 |
| 3,873,557 | 3/1975 | Abblard et al. | 546/301 |
| 3,948,919 | 4/1976 | Nakanishi | 546/115 |
| 3,952,101 | 4/1976 | Jen et al. | 424/263 |
| 4,011,231 | 3/1977 | Carroll et al. | 546/300 |
| 4,031,108 | 6/1977 | Nakanishi | 546/268 |

OTHER PUBLICATIONS

Benderly et al., Can. J. Chem. 56, pp. 2673-2676, (1978).

Primary Examiner—Alan L. Rotman
Attorney, Agent, or Firm—Charles J. Knuth; Albert E. Frost; Robert K. Blackwood

[57] ABSTRACT

Processes and intermediates useful in the preparation of bronchodilator compounds of the formula

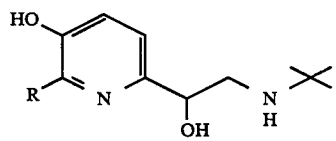

wherein R is hydrogen, methyl or hydroxymethyl are described. Those compounds wherein R is H or CH$_3$ have been found to have further utility as intermediates for pirbuterol (wherein R is hydroxymethyl).

3 Claims, No Drawings

3-ACETOXY OR BENZYLOXY-2-ACETOXYMETHYL-6-[1-ACETOXY-2-(N-TERT-BUTYLACETAMIDO)ETHYL]PYRIDINE INTERMEDIATES

CROSS REFERENCE TO RELATED APPLICATION

This application is a division of co-pending application Ser. No. 340,172, pending filed Jan. 18, 1982, which is a division of application Ser. No. 232,923, filed Feb. 9, 1981, now abandoned.

BACKGROUND OF THE INVENTION

This invention relates to processes for the preparation of pirbuterol and analogs, compounds of the formula

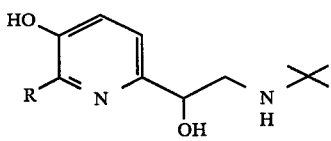

wherein R is hydrogen, methyl or hydroxymethyl and the intermediates therefor, including processes for the conversion of compounds of the formula (I) wherein R is hydrogen or methyl into pirbuterol [formula I, wherein R is hydroxymethyl].

Pirbuterol and its bronchodilator activity were originally described by Barth in a series of U.S. Pat. Nos. (3,700,681; 3,763,173; 3,772,314; 3,786,160). At that time, pirbuterol was synthesized as follows:

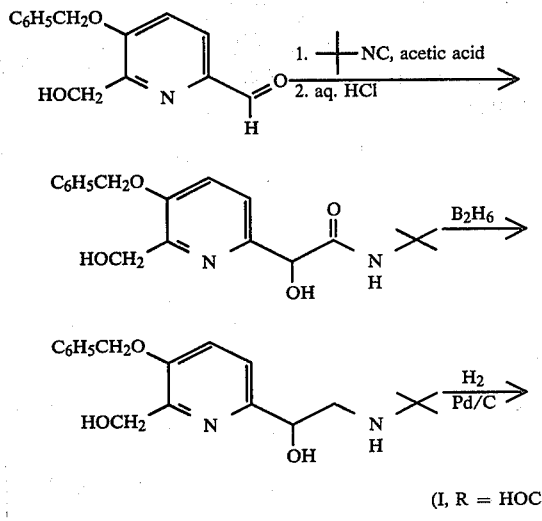

The pirbuterol analogs of the formula I, wherein R is hydrogen, methyl, or methanesulfonylmethyl, and their bronchodilator activity, were disclosed by Jen and Kaiser in U.S. Pat. No. 3,952,101. These compounds were prepared from the corresponding aldehydes by a reaction sequence fully analogous with that of the earlier pirbuterol process.

Subsequently, an alternative, preferred process for the synthesis of pirbuterol was described by Nakanishi (U.S. Pat. Nos. 3,948,919; 4,031,108), exemplified as follows:

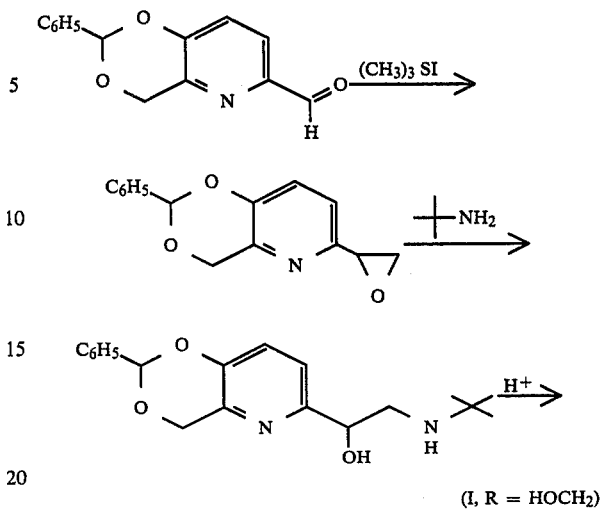

Improvements and alternatives to this process have also been described, viz., isolation of the pirbuterol precursor as a maleate salt (Carroll et al., U.S. Pat. No. 4,011,231) and hydrogenolysis rather than hydrolysis as the final stage (Argentina Pat. No. 214005, Luxembourg Pat. No. 79564).

The latter process still suffers from the disadvantage of generating noxious sulfide by-products in the preparation of epoxide. Even under the best of conditions, traces of sulfur can carry through and increase the catalyst level when protecting groups are removed by hydrogenolysis, the preferred route when the free base form of pirbuterol is desired. Furthermore, the epoxide is relatively unreactive towards the tertbutylamine reagent, even under pressure at elevated temperatures requiring large excess of the reagent and a relatively long time to achieve complete reaction.

A further disadvantage of the improved process is the polar nature of intermediate amino alcohol, making this intermediate difficult to isolate in pure form.

Recently pirbuterol has been discovered to also have utility for the treatment of congestive heart failure (Taylor, U.S. Pat. No. 4,175,128).

In a chemical transformation related to one of the process steps of the present invention, Benderly et al., [Can. J. Chem. 56, pp. 2673–2676 (1978)] have reported the conversion of 2-vinylpyridine to 2-(1,2-epoxyethyl)-pyridine N-oxide by the action of m-chloroperbenzoic acid on 2-vinylpyridine.

SUMMARY OF THE INVENTION

The present invention provides facile methods for the synthesis of pirbuterol and analogs, summarized below as Processes A-D.

PROCESS A

This process involves the following chemical steps:

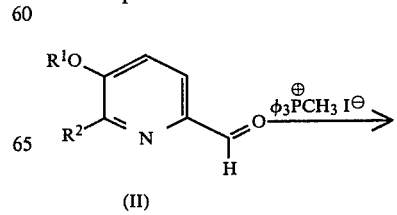

-continued

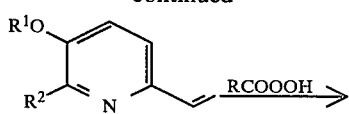

(III)

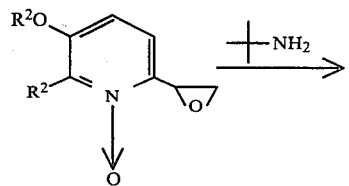

(IV)

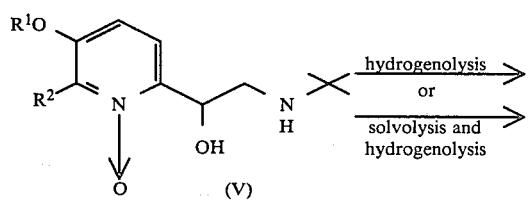

(V)

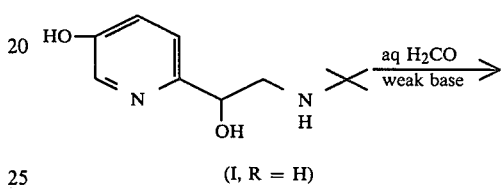

(I)

wherein in formula (I) R is hydrogen, methyl or hydroxymethyl and in formulae (II) to (V), $R^1$ is benzyl and $R^2$ is hydrogen or methyl; or $R^1$ and $R^2$ are taken together and are

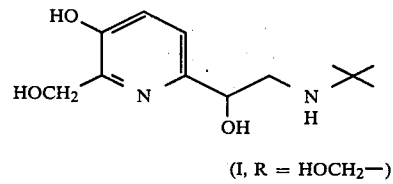

This improved process avoids co-production of noxious sulfur compounds in the epoxidation step, permits epoxide opening under milder conditions, thus affording better quality intermediate and generally permits lower catalyst levels when hydrogenolysis is a later process step.

PROCESS B

This process involves hydroxymethylation as follows:

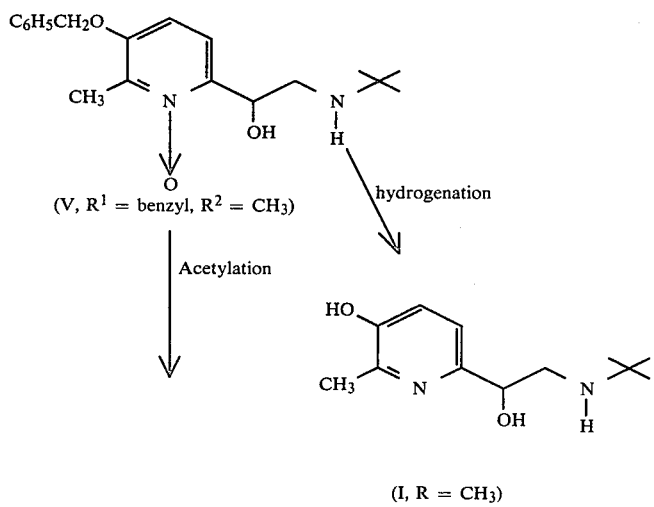

This process permits a single step synthesis from a precursor having potential commercial availability by dint of its own biological activity.

PROCESS C

This process involves the following alternative chemical steps:

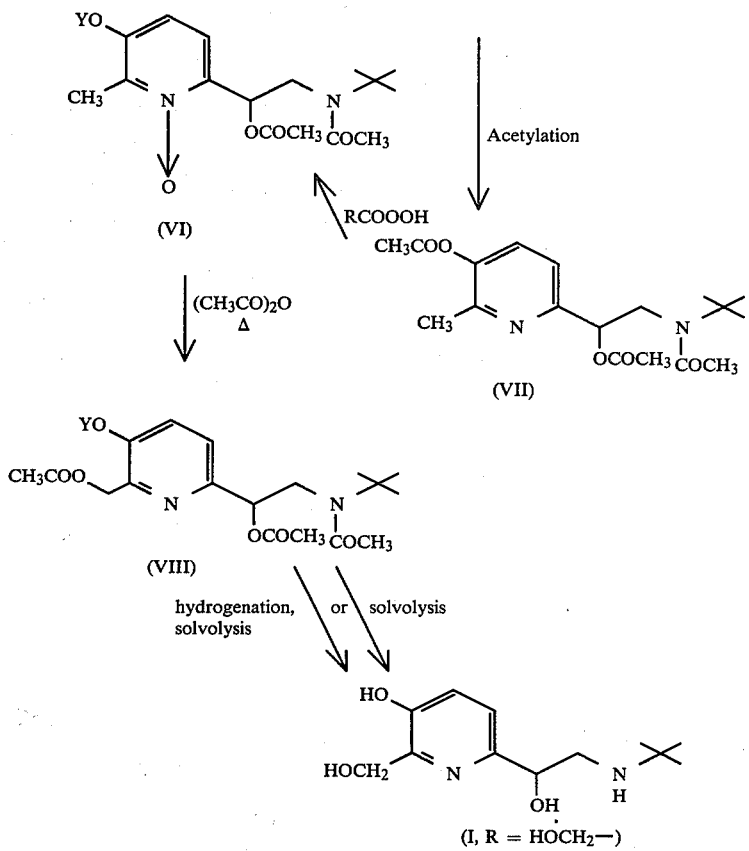

wherein in the formulae (VI) and (VIII), Y is benzyl or acetyl.

This process also permits facile synthesis of pirbuterol from a compound having potential commercial availability; or alternatively, taking advantage of the intermediate (V, $R^1$=benzyl, $R^2$=$CH_3$) of Process A which is easily produced from readily available pyridine carbaldehyde (II, $R^1$=benzyl, $R^2$=$CH_3$).

PROCESS D

This process involves the following simple chemical steps:

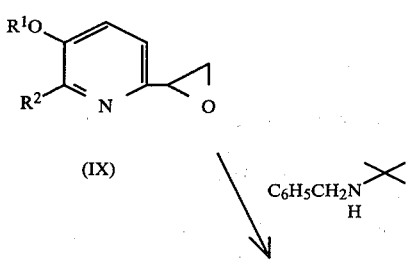

wherein $R^1$ and $R^2$ are as defined above.

This process provides a less polar intermediate (X), more readily isolated and purified by standard partition, extraction and crystallization techniques than the corresponding intermediate lacking the benzyl group or the aminoalcohol side chain.

DETAILED DESCRIPTION OF THE INVENTION

The processes of the present invention have been summarized above in flowsheet form. The processes are hereinafter described in greater detail, while referring to the flow diagrams above.

Process A

The conversion of pyridinecarbaldehyde (II) to the vinylpyridine (III) is-accomplished by the action of a molar excess (e.g. 2 equivalents) of a quaternarymethylphosphonium halide such as methyltriphenylphosphonium iodine in a reaction-inert organic solvent such as toluene in the presence of about one molar equivalent of sodium hydroxide at 0°-50° C., conveniently at ambient temperature.

The conversion of the vinylpyridine (III) to the exposide-N-oxide (IV) is accomplished by the action of at least two molar equivalents of peracid, conveniently m-chloroperbenzoic acid, in a reaction-inert solvent such as methylene chloride at a temperature of 10°-60° C., conveniently at the reflux temperature of methylene chloride. The epoxide-N-oxide (IV) is also prepared by peracid oxidation of epoxide compounds of the formula

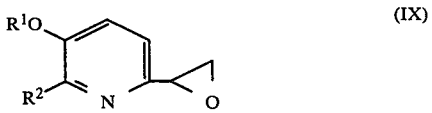

wherein $R^1$ and $R^2$ are as hereinbefore defined. Preparation of compounds wherein $R^1$ is benzyl and $R^2$ is hydrogen or methyl is described in the Specific Examples detailed below. The compound wherein $R^1$ and $R^2$ are taken together is described in the above U.S. Patents to Nakanishi.

The conversion of the epoxide-N-oxide (IV) to the amine (V) is readily accomplished using an excess of tert-butylamine, optionally in the presence of an inert diluent such as methanol, at 20° to 70° C. In comparison to the corresponding tert-butylamine epoxide opening of a compound of the formula (IX), relatively mild conditions (lower temperature, shorter reaction time, less excess of reagent) are required, resulting in lowered cost and generally cleaner intermediate product.

In any case, the final stage of Process A, conversion of the amine (V) to the desired end-products (I), can be accomplished by hydrogenolysis over a noble metal catalyst in a reaction-inert solvent. The temperature of the hydrogenolysis is not critical, e.g. 0°-100° C. can be used, but is conveniently carried out at ambient temperature avoiding the costs of cooling or heating. The pressure of the hydrogenation is also not critical (e.g. pressures of subatmospheric to 200 psi or more can be used), but relatively low pressures (e.g. 20-70 psi) are generally used, since the reaction proceeds at a resonable rate without requiring the more elaborate equipment characteristic of high pressure hydrogenations. The noble metal catalysts employed in the present invention include platinum, palladium, ruthenium and rhodium, either of the supported or non-supported type, as well as the known catalytic compounds thereof such as oxides, chlorides, etc. Examples of suitable catalyst supports include carbon and barium sulfate. In the present instance a preferred catalyst is palladium on carbon (1 to 10% of Pd by weight). The hydrogenation solvent is also not critical. It should not react with reactants or product (i.e. it should be reaction inert). Suitable solvents include ($C_1$-$C_4$) alcohols, particularly methanol which can serve as solvent for formation of the hydrochloride salt which is a a common form of pirbuterol.

Other solvents such as tetrahydrofuran or dioxane can, of course, be used either alone or in combination with each other and/or the above mentioned alcohols. Higher boiling solvents, (e.g. ethylene glycol, diglyme) can also be used, but are not favored because more energy is required to removed them from the reaction mixture. In order to minimize or avoid hydrogenolysis of the 1-hydroxy-2-tert-butylaminoethyl side chain to a 2-tert-butylethyl group, it is preferred that the hydrogenolysis be carried out in the presence of a small amount of water (e.g. from 1 to 30 molar equivalents). In the particular case of preparing pirbuterol, the reaction is interrupted when the theoretical amount of hydrogen is consumed. If desired hydrogenation can be continued (optimally in the presence of acid, e.g. HCl) so as to carry out the following transformation:

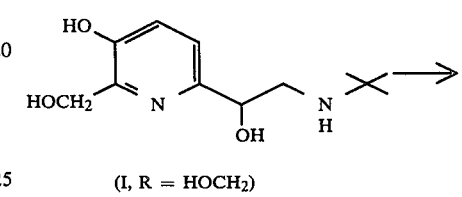

(I, R = $HOCH_2$)

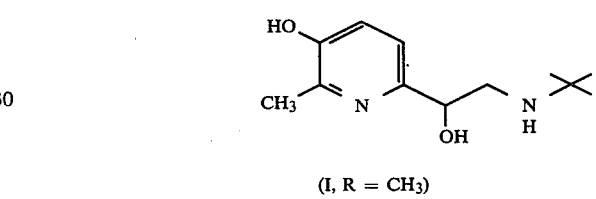

(I, R = $CH_3$)

When $R^1$ and $R^2$ are taken together, the conversion of the amine (V) is alternatively carried out by two stage solvolysis and hydrogenation as follows:

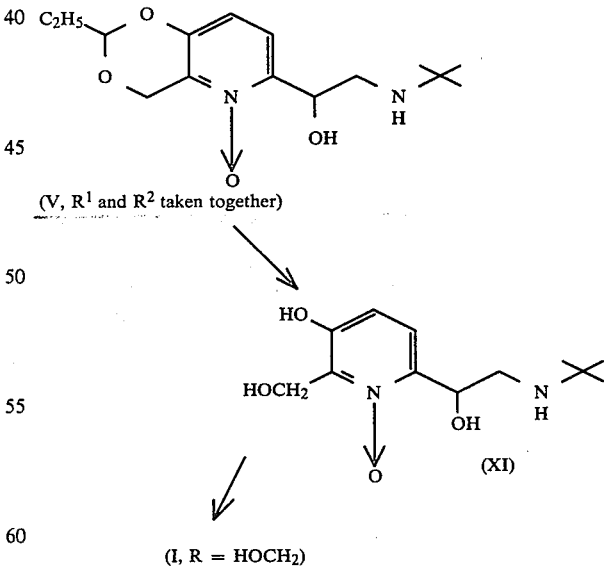

(I, R = $HOCH_2$)

The solvolysis is carried out in aqueous or alcoholic media, with or without cosolvents, usually in the presence of an acid catalyst. Particularly suitable is a combination of methanol and hydrogen chloride from which the intermediate is readily isolated in the form of the hydrochloride salt. Temperature is not critical; e.g.

temperature of 0°–50° C. or higher can be used, but the reaction is conveniently carried out at ambient temperature. Acid catalyzed solvolysis is preferred over base catalyzed solvolysis, since the products have some tendency to degrade under basic conditions. When solvolysis is used to remove the benzhydryl group, the final stage hydrogenolysis is carried out according to the methods detailed above, preferrably on the free base form compound (XI) in order to avoid over hydrogenation of the 6-hydroxymethyl group to methyl.

Process B

The hydroxmethylation of the compound (I, R=H) to yield pirbuterol (I, R=HOCH$_2$) is readily carried out by heating the former in excess aqueous formaldehyde in the presence of an excess of a weak base. Reaction temperatures in the range 85°–105° C. are generally used, the reflux temperature of the reaction mixture being well-suited. The weak base should be one which does not react to any significant degree with starting materials, or product, or cause a high degree of polymerization of the formaldehyde. Tertiary aliphatic amines, conveniently readily available and inexpensive triethylamine, are well suited as the weak base catalyst for this reaction.

The starting material is available by methods detailed in the Jen and Kaiser U.S. Patent cited above, or preferably by methods detailed elsewhere herein.

Process C

The hydrogenation of the amine (V, R$^1$=benzyl, R$^2$=methyl) to the compound (I, R=methyl) is described above.

The acetylations to produce compounds of the formulae (VI) and (VII) are carried out under mild conditions with at least 2 to 3 molar equivalents, respectively, of an acetylating agent (e.g. acetyl chloride, acetic anhydride, in the presence of a tertamine such as triethylamine, in an amount usually at least molarly equivalent to the acetylating agent. The reaction is carried out in an inert solvent, such as methylene chloride, ethyl acetate or the like. The temperature is non-critical in the case of the acetylation of (I, R=methyl) and can be in the range of 0°–100° C. When ethyl acetate is used as solvent, it is convenient to employ the reflux temperature of the reaction mixture. However, in the case of the acetylation of (V, R$^1$=benzyl, R$^2$=methyl), lower temperatures, e.g. 0°–30° C., are preferred in order to avoid or minimize side reactions involving the N-oxide group.

The oxidation of the pyridine compound (VII) to the pyridine-N-oxide (VI) is carried out by the action of a peracid, using the peracid oxidation methodology detailed above.

The key reaction in the sequence, rearrangement of the pyridine-N-oxide (VI) to the acetoxymethylpyridine (VIII) is readily carried out by heating in excess acetic anhydride. The temperature employed is in the range 120°–160° C., conveniently at the reflux temperature of the reaction mixture (about 140° C.), but preferably under elevated pressure when the reaction is carried out at or above the atmospheric boiling point of the reaction mixture, thus avoiding the unnecessary cost of condensing and reheating acetic anhydride.

The final solvolysis, or hydrogenolysis-solvolysis stages are carried out under the same hydrogenolysis and solvolysis conditions detailed above in connection with Process C.

The starting material (V, R$^1$=benzyl, R$^2$=methyl) is available according to Process C. The intermediate compound (I) is alternatively available according to Jen and Kaiser as cited above, or by other methods detailed elsewhere herein.

Process D

The convention of the pyridine-epoxide (IX) to benzylamine (X) is accomplished by warming the epoxide with at least one equivalent of N-tert-butylbenzylamine, with or without the presence of a reaction inert diluent. The temperature will generally be elevated (e.g. 50°–100° C.) in order to complete the reaction in a reasonable time period. Suitable diluents are (C$_1$–C$_4$) lower alkanols such as methanol, dioxane, 1,2-dimethoxyethane, and the like. Methanol is particularly well suited as diluent, under pressure at a temperature of at or above the atmospheric boiling point of methanol (e.g. 65°–80° C.).

In any case, the benzylamine (X) can be hydrogenolyzed under the conditions detailed above under Process C, to produce the compound I. When R$^1$ and R$^2$ are taken together, the benzylidine group can be first removed by solvolysis, producing

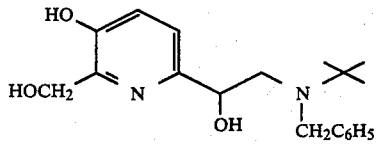

and the benzyl group removed in the final stage of the process, again according to conditions detailed above.

The starting material (IV) for Process D is available in the literature detailed above or by methods provided elsewhere herein.

Another advantageous process for the synthesis of pirbuterol and its analogs is as follows:

PROCESS E

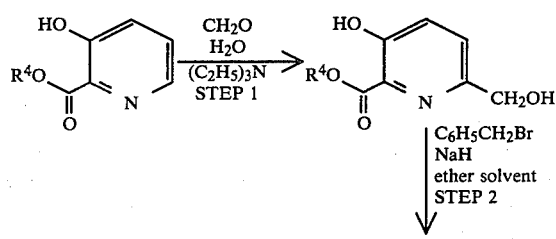

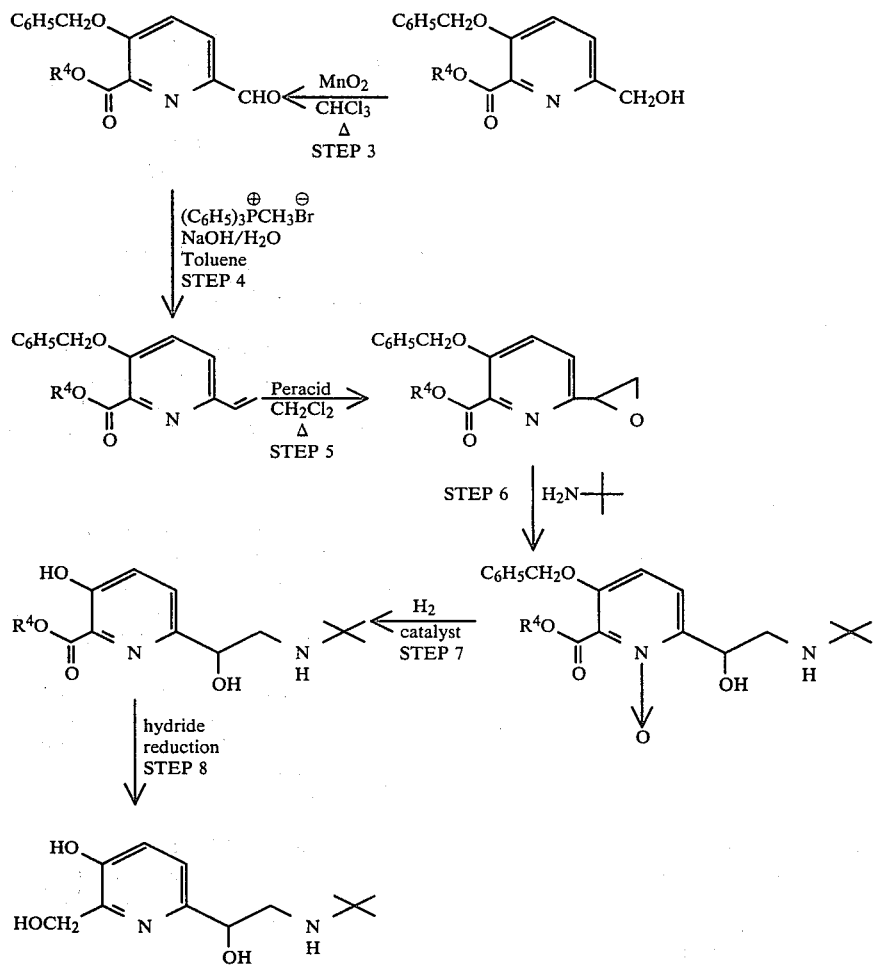

wherein $R^4$ is $(C_1-C_4)$ alkyl.

The step 1 hydroxymethylation is carried out under conditions described above (Process B). Steps 2 and 3 are carried out under conditions described earlier for benzylation of 2,6-bis-(hydroxymethyl)-3-hydroxypyridine and oxidation of 2,6-bis-(hydroxymethyl)-3-benzyloxypyridine (Barth, U.S. Pat. No. 3,700,681). Steps 4 to 7 are carried out under conditions described above in connection with Process A. The final hydride reduction, step 8, is accomplished by the action of lithium aluminum hydride in an ether solvent such as ether, tetrahydrofuran or 1,2-dimethoxyethane, sodium aluminum di(2-methoxyethoxy) dihydride (Red-Al) in a solvent such as warm benzene, lithium borohydride in refluxing tetrahydrofuran, or diborane in an ether solvent as defined immediately above.

The present invention is illustrated by the following examples. However, it should be understood that the invention is not limited to the specific details of these examples.

EXAMPLE 1

2-Phenyl-6-vinyl-4H-1,3-dioxino[5,4-b]pyridine (II, $R^1$ and $R^2$ taken together)

In a two liter 3-neck, round bottom flask, fitted with a mechanical stirrer, a thermometer and a reflux condenser, a heterogeneous mixture of 2-phenyl-4H-1,3-dioxino[5,4-b]pyridine-6-carbaldehyde (24.1 g., 0.1 mole) sodium hydroxide (24.0 g., 0.6 mole) and methyltriphenylphosphonium bromide (71.5 g., 0.2 mole) in toluene (200 ml.) and water (600 ml.) was stirred at room temperature for 24 hours. The toluene layer was separated and the aqueous layer was washed with toluene (100 ml.). The combined toluene layers were dried over anhydrous magnesium sulfate. The toluene solution was then passed through a 10 mm. pad of silica gel which was then washed with 1 liter of ether/hexane solution (v/v 3:2). Evaporation of the solvents on a rotary evaporation in vacuo gave the crystalline 2-phenyl-6-vinyl-4H-1,3-dioxino [5,4-b]pyridine, 14.3 g. (59%); m.p. 54°–57° C.; mass spec (70 eV) m/e 211 (M+), 134, 133, 132, 106, 105, 104.

Anal. Calcd. for $C_{15}H_{13}NO_2$: C, 75.29; H, 5.48; N, 5.86; Found: C, 75.42; H, 5.01; N, 6.01.

EXAMPLE 2

6-(1,2-Epoxyethyl)-2-phenyl-4H-1,3-dioxino[5,4-b]-pyridine N-oxide (III, $R^1$ and $R^2$ taken together)

Method A

In a 4-neck 500 ml., round bottom flask, fitted with a reflux condenser, a mechanical stirrer/magnetic stirring bar and a thermometer, was placed 2-phenyl-6-vinyl-4H-1,3-dioxino[5,4-b]pyridine (8.0 g., 0.033 mole) in methylene chloride (250 ml.). The solution was treated portion wise with m-chloroperbenzoic acid (20.0 g., 0.116 mole). When all of the peracid was added, the solution was heated at reflux overnight. Upon cooling m-chlorobenzoic acid crystallized from the reaction mixture and was filtered off. The filtrate was washed with aqueous sodium bicarbonate solution, dried over anhydrous magnesium sulfate and evaporated in vacuo to give the crude product (5.1 g.) which was recrystallized from ethyl acetate to give 6-(1,2-epoxyethyl)-2-phenyl-4H-1,3-dioxino[5,4-b]pyridine N-oxide (1.9 g., 21%), m.p. 180°–181.5° C. (dec.); NMR (CDCl$_3$) delta 7.28 (m, 5H), 6.82 (q, 2H), 5.82 (s, 1H), 5.05 (s, 2H), 4.40 (d of d, 1H), 3.18 (d of d, 1H), 2.97 (d of d, 1H); mass spec (70 eV), m/e 271 (M+), 241 (M—O, CH$_2$), 206, 165, 149, 132, 107, 105, 101, 82, 80, 79, 77.

Anal. Calcd. for C$_{15}$H$_{13}$NO$_4$: C, 66.41; H, 4.83; N, 5.16; Found: C, 66.36; H, 4.43; N, 4.79.

Method B

In a two liter 4-neck round bottom flask fitted with a thermometer, a magnetic stirring bar/stirrer and a reflux condenser was placed 6-(1,2-epoxyethyl)-2-phenyl-4H-1,3-dioxino[5,4-b]pyridine (125.7 g., 0.49 mole) in methylene chloride (1 liter). In several portions, m-chloroperbenzoic acid (109 g., 0.63 mole) was added to the stirred solution. Over a 30 minute period an exotherm to 32° C. was observed. The reaction mixture was allowed to stir at room temperature for 24 hours during which m-chlorobenzoic acid precipatated. After removing the acid by filtration, the filtrate was washed with aqueous sodium bicarbonate, dried over anhydrous magnesium sulfate, filtered and evaporated. The residual solid was recrystallized from isopropanol to give the N-oxide 65.5 g. (49%); m.p. 182°–184° C. (dec); NMR identical with epoxy N-oxide prepared by Method A of this Example.

EXAMPLE 3

6-(1-Hydroxy-2-tert-butylaminoethyl)-2-phenyl-4H-1,3-dioxino[5,4-b]pyridine N-oxide (IV, R$^1$ and R$^2$ are taken together)

To 15.0 g. (0.055 mole) of 6-(1,2-epoxyethyl)-2-phenyl-4H-1,3-dioxino[5,4-b]pyridine N-oxide in 200 ml. of methanol was added 30 ml. tert-butylamine and the resulting reaction mixture was heated to the reflux temperature for 3 hours. Solvent and excess tert-butylamine were removed in vacuo to give 13.4 g. (73.6%) of 6-(1-hydroxy-2-tert-butylaminoethyl)-2-phenyl-4H-1,3-dioxino[5,4-b]pyridine N-oxide after recrystallization from ethyl acetate: m.p. 165°–168° C.

Anal. Calcd for C$_{19}$H$_{24}$N$_2$O$_4$: C, 66.20; H, 6.97; N, 8.13; Found: C, 66.12; H, 6.59; N, 8.11.

EXAMPLE 4

3-Hydroxy-6-(1-hydroxy-2-tert-butylaminoethyl)-2-hydroxymethylpyridine N-oxide Dihydrochloride Gaseous hydrogen chloride was bubbled into a solution of 5.0 g. (0.0145 mole) of 6-(1-hydroxy-2-tert-butylaminoethyl)-2-phenyl-4H-1,3-dioxino[5,4-b]-pyridine N-oxide in 100 ml. of methanol at 10° C. After stirring overnight the solvent was removed in vacuo. The residue was triturated with ethyl acetate and filtered to give 3-hydroxy-6-(1-hydroxy-2-tert-butylaminoethyl)-2-hydroxymethylpyridine N-oxide dihydrochloride (3.9 g., 81%); m.p. 177°–179° C. (dec.).

Anal. Calcd for C$_{12}$H$_{22}$N$_2$O$_4$Cl$_2$: C, 43.77; H, 6.73; N, 8.51; Found: C, 43.76; H, 6.53, N, 8.49;

EXAMPLE 5

3-Hydroxy-6-(1-hydroxy-2-tert-butylaminoethyl)-2-methylpyridine dihydrochloride

Into a 500 ml. Parr bottle there was introduced 13.4 g. (0.04 mole) of 3-hydroxy-6-(1-hydroxy-2-tert-butylaminoethyl)-2-hydroxymethylpyridine N-oxide dihydrochloride and 6.5 g. of 5% palladium on carbon catalyst in 150 ml. of methanol. Under a hydrogen pressure of 43 psi the mixture was shaken at room temperature for two days. The catalyst was removed by filtration under a nitrogen atmosphere followed by removal of the solvent in vacuo to give an oil which was triturated with isopropanol to induce crystallization. Filtration of the resulting solid afforded 3-hydroxy-6-(1-hydroxy-2-tert-butylaminoethyl)-2-methylpyridine dihydrochloride, 10.0 g. (85%) m.p. 226°–228.5° C. (dec.); NMR (DMSO d$_6$) delta 7.80 (q, 2H, pyridyl H), 5.40 (br m, 1H); 3.30 (br m, 2H), 2.60 (s, 3H, 2-CH$_3$) and 1.35 (s, 9H, t-Bn).

Anal. Calcd for C$_{12}$H$_{22}$N$_2$O$_2$Cl$_2$.0.5H$_2$O: C, 47.06; H, 7.57; N, 9.11; Found: C, 47.20; H, 7.13; N, 9.21.

EXAMPLE 6

Pirbuterol Hydrochloride [3-Hydroxy-6-(1-hydroxy-2-tert-butylaminoethyl)-2-hydroxymethylpyridine Dihydrochloride]

Into a 500 ml. Parr bottle there were introduced 970 mg. (0.0028 mole) of 6-(1-hydroxy-2tert-butyl-aminoethyl)-2-phenyl-4H-1,3-dioxino[5,4-b]pyridine N-oxide and 450 mg. 5% palladium on carbon catalyst in 25 ml. of methanol. Under a hydrogen pressure of 40 psi the mixture was shaken at room temperature for 17 hours. The catalyst was removed by filtration under a nitrogen atmosphere, the methanol solution was diluted with an equal volume of ethyl acetate and hydrogen chloride gas was introduced into the solution. Without heating, the resulting solution was concentrated in vacuo until the product began to precipitate. After stirring at room temperature for several hours, the white solid was collected by filtration and air-dried to give pirbuterol hydrochloride (450 mg., 51%); m.p. 180°–184° C. (dec.) which is identical by thin-layer chromatography (ethyl acetate/methanol/diethylamine [30:15:5 (v/v)], and nuclear magnetic resonance spectroscopy to the product in U.S. Pat. No. 3,700,681.

EXAMPLE 7

5-Benzyloxy-2-vinylpyridine

In a two liter 3-neck round bottom flask fitted with a mechanical stirrer, thermometer and a water-cooled reflux condenser was placed 23.4 g. (0.11 mole) of 5-benzyloxypyridine-2-carbaldehyde, 78.5 g. (0.22 mole) of methyltriphenylphosphonium bromide and 26.5 g. (0.66 mole) of sodium hydroxide pellets in 250 ml. of toluene and 665 ml. of water. The reaction mixture was stirred at room temperature for 15 hours. The toluene layer was separated and saved. The aqueous layer was washed with toluene and the combined toluene layers are filtered through a 4"×6" pad of silica gel to remove triphenylphosphate. The pad was successively washed with toluene, then ether/hexane (3.2) to remove the desired product. The organic solutions were combined, dried over anhydrous magnesium sulfate, filtered and evaporated in vacuo to give 5-benzyloxy-2-vinylpyridine as a yellow oil (20.5 g., 73.7%); NMR (CDCl$_3$) 8.15

(m, 1H, H₆), 7.16 (s, 5H, C₆H₅—), 7.00 (m, 2H, H₃ and H₄), 6.67 (d of d, 1H, oletin H), 5.95 (d of d, 1H, oletin H), 5.15 (d of d, 1H, oletin H) and 4.90 (3, 2H, CH₂).

EXAMPLE 8

5-Benzyloxy-2-(1,2-expoxyethyl)pyridine N-Oxide

In a 3-neck 100 ml. round bottom flask fitted with a thermometer, magnetic stirrer/stirring bar and reflux condenser is placed 1.00 g. (0.005 mole) of 5-benzyoxy-2vinylpyridine in 30 ml. of methylene chloride. To this vigorously stirred solution m-chloroperoxybenzoic acid (2.00 g., 0.01 mole) was added in one portion. The resulting solution was heated to reflux for 12 hours. Workup in the same manner as Example 2 gave 5-benzyloxy-2-(1,2-epoxyethyl)pyridine N-oxide [0.50 g., (42%)]; m.p. 108°–110° C. (dec.); NMR (CDCl₃) delta 8.00 (d, 1H, H₆), 7.33 (m, 5H, phenyl H), 7.30-7.10 (m, 2H, H₃ and H₄), 5.05 (s, 2H, $\underline{CH_2}$ of benzyl), 4.47 (m, 1H, epoxide CH), 3.23 (d of d, 1H, epoxide CH) and 2.67 (m, 1H, epoxide H), mass spectrum (70 eV) m/e 243 (M⁺), 152 (M⁺-CH₂C₆H₅), 91 (C₇H₇⁺).

EXAMPLE 9

5-Benzyloxy-2-(1-hydroxy-2-tert-butylaminoethyl)-pyridine N-oxide

To 0.50 g. (0.0042 mole) of [5-benzyloxy-2-(1,2-epoxyethyl) pyridine N-oxide] in 20 ml. of methanol was added 0.5 ml. tert-butylamine and the resulting mixture heated to the reflux temperature for 4 hours. Solvent and excess tert-butylamine were removed in vacuo to give 280 mg. (43%) of the desired product after recrystallization from ether/ethyl acetate; m.p. 148°–150° (dec.). Mass spec (70 eV) m/e 300 (M-16), m/e 243 [M-H₂NC(CH₃)₃]; NMR (DMSO d₆) delta 7.90 (d, 1H, H₆), 7.30 (m, 6H, benzyl C₆H₅ and H₄), 7.00 (m, 1H, H₃), 5.07 (m, 3H, φ$\underline{CH_2}$ and

4.33 (m, 2H,

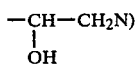

and 1.13 [s, 9H, C($\underline{CH_3}$)₃]; ir (KBr) 1171 (N⁺-O⁻).

EXAMPLE 10

5-Hydroxy-2-(1-hydroxy-2-tert-butylaminoethyl)-pyridine

Into a 250 ml. Parr bottle there were introduced 250 mg. (0.79 mmole) of 5-benzyloxy-2-(1-hydroxy-2-tert-butylaminoethyl)pyridine N-oxide and 125 mg. of 5% palladium on carbon of 45 psi. The mixture was shaken at room temperature for 6 hours. The catalyst was removed by filtration under a nitrogen atmosphere followed by removal of the solvent in vacuo to give the product which was triturated with isopropanol and filtered. In this manner, there was obtained 175 mg. (75%) of 5-hydroxy-2-(1-tert-butylaminoethyl)pyridine as white crystals, m.p. 165°–168° C. (decomp).

EXAMPLE 11

5-Benzyloxy-2-(1,2-epoxyethyl)pyridine

In a 500 ml. 3-neck round bottom flask fitted with a thermometer and a mechanical stirrer, there was introduced 26.7 g. (0.13 mole) of trimethylsulfonium iodide in 175 ml. of N,N-dimethylformamide. The stirred solution was cooled to 0°–5° C. in an ice bath and 21.3 g. (0.39 mole) of sodium methoxide was added in one portion. After stirring the reaction mixture for 10 minutes at 0° there was added portionwise over a 15 minute period 21.3 g. (0.1 mole) of 5-benzyloxypyridine-2-carbadehyde. When the addition was completed the reaction mixture was stirred at 0° C. for 15 minutes, then poured into ice cold water (1 liter). The aqueous solution was extracted with two 250 ml. portions of ether. The ether layers were separated, combined and washed with two 250 ml. portions of water, then dried over anhydrous magnesium sulfate, filtered and evaporated in vacuo to give an oil which rapidly crystallized to afford 20.7 g. (91%) of 5-benzyloxy-2-(1,2-epoxyethyl)-pyridine, m.p. 45°–47.5° C. (recrystallized from hexanes).

EXAMPLE 12

5-Benzyloxy-2-(1-hydroxy-2-tert-butylaminoethyl)pyridine

To a solution of 20.7 g. (0.091 mole) of 5-benzyloxy-2-(1,2-epoxyethyl)pyridine in 250 ml. of methanol, 25 ml. of tert-butylamine was added and the resulting solution was heated at the reflux temperature for 2.5 hours. The solvent and the excess tert-butylamine were evaporated in vacuo to give after recrystallization from hexanes, 17.3 g. (61%) of 5-benzyloxy-2-(1-hydroxy-2-tert-butylaminoethyl)pyridine; m.p. 69°–73° C.

Anal. Calcd. for $C_{18}H_{24}O_2N_2$: C, 71.97; H, 8.05; N, 9.33; Found: C, 71.86; H, 7.96; N, 9.26.

EXAMPLE 13

5-Hydroxy-2-(1-hydroxy-2-tert-butylaminoethyl)pyridine

By the procedure of Example 10, 5-benzyloxy-2-(1-hydroxy-2-tert-butylaminoethyl)pyridine is hydrogenolyzed to produce 5-hydroxy-2(1-hydroxy-2-tert-butylaminoethylpyridine.

EXAMPLE 14

Pirbuterol Hydrochloride

A solution of 5-hydroxy-2-(1-hydroxy-2-tert-butylaminoethyl)pyridine (0.500 g., 0.00238 mole) in 5 ml. of aqueous 38% formaldehyde solution and 1 ml. of triethylamine was heated at the reflux temperature overnight. An additional 5 ml. of aqueous formaldehyde solution was added and heating at the reflux temperature was continued for 6 hours. The solvents were evaporated in vacuo to give the crude product which was isolated by dissolving it in a minimum volume of cold methanol and saturating the cold solution with dry hydrogen chloride to give 0.52 g. (70%) of pirbuterol hydrochloride m.p. 174°–176° (dec.).

EXAMPLE 15

3-Benzyloxy-2-methyl-6-vinylpyridine

By the procedure of Example 7, 3-benzyloxy-2-methylpyridine-6-carbaldehyde is converted to 3-benzyloxy-2-methyl-6-vinylpyridine.

EXAMPLE 16

3-Benzyloxy-2-methyl-6-(1,2-epoxyethyl)pyridine N-Oxide

By the procedure of Example 8, 3-benzyloxy-2-methyl-6-vinylpyridine is converted to 3-benzyloxy-2-methyl-6-(1,2-epoxyethyl)pyridine N-oxide.

EXAMPLE 17

3-Benzyloxy-2-methyl-6-(1-hydroxy-2-tert-butylaminoethyl)pyridine N-Oxide

By the procedure of Example 9, 3-benzyloxy-2-methyl-6-(1,2-epoxyethyl)pyridine N-oxide is converted to 3-benzyloxy-2-methyl-6-(1-hydroxy-2-tert-butylaminoethyl)pyridine N-oxide.

EXAMPLE 18

3-Hydroxy-6-(1-hydroxy-2-tert-butylaminoethyl)-2-methylpyridine

By the procedure of Example 5, 3-benzyloxy-2-methyl-6-(1-hydroxy-2-tert-butylaminoethyl)pyridine is also hydrogenated to yield the same 3-hydroxy-6-(1-hydroxy-2-tert-butylaminoethyl)-2-methypridine.

EXAMPLE 19

3-Acetoxy-2-methyl-6-[1-acetoxy-2-(N-tert-butylacetamido)ethyl]pyridine

To a suspension of 2-(1-hydroxy-2-tert-butylaminoethyl)-5-hydroxy-6-methylpyridine dihydrochloride (7.70 g., 0.026 mole) in 300 ml. of ethyl acetate and 7.7 ml. of triethylamine, 10.8 ml. of acetic anhydride was added and the solution was heated at the reflux temperature for 30 hours. An additional 5 ml. of acetic anhydride was added to the reaction mixture and heating was continued for 24 hours, then allowed to cool to room temperature. The reaction mixture was poured into aqueous sodium bicarbonate solution (100 g. NaHCO$_3$ in 700 ml. H$_2$O) and the resulting mixture was stirred for 1 hour. The ethyl acetate layer was separated, washed with aqueous sodium bicarbonate, then water and dried over magnesium sulfate. Evaporation of the dried ethyl acetate solution in vacuo gave 3-acetoxy-2-methyl-6-[1-acetoxy-2-(N-tert-butylacetamido)ethyl]pyridine, the product 6.0 g. (66%); m.p. 124.5°–127.5° C.

Anal. Calcd. for C$_{18}$H$_{26}$N$_2$O$_5$: C, 61.70; H, 7.48; N, 8.00; Found: C, 61.93; H, 7.39; N, 8.44.

EXAMPLE 20

3-Acetoxy-2-methyl-6-[1-acetoxy-2-(N-tert-butylacetamido)ethyl]pyridine N-Oxide

A solution of 3-acetoxy-2-methyl-6-[1-acetoxy-2-(N-tert-butylacetamido)ethyl]pyridine (5.50 g., 0.0157 mole) and m-chloroperbenzoic acid (85% technical grade, 3.90 g., 0.0192 mole) in 150 ml. of chloroform was stirred at room temperature for 24 hours. After washing the reaction mixture with two portions of aqueous sodium bicarbonate solution, the dried (MgSO$_4$) chloroform solution was evaporated to give 2.9 g. (50%) of 3-acetoxy-2-methyl-6-[1-acetoxy-2-(N-tert-butylacetamido)ethyl]pyridine N-oxide; m.p. 113°–116.5° C. after recrystallization from ether.

Anal. Calcd. for C$_{18}$H$_{26}$N$_2$O$_6$: C, 59.00; H, 7.15; N, 7.65; Found: C, 59.25; H, 7.08; N, 8.14.

EXAMPLE 21

3-Acetoxy-2-acetoxymethyl-6-[1-acetoxy-2-(N-tert-butylacetamido)ethyl]pyridine

A solution of 1.0 g. (0.0027 mole) of 3-acetoxy-2-methyl-6-[1-acetoxy-2-(N-tert-butylacetamido)ethyl]pyridine N-oxide in 10 ml. of acetic anhydride was heated at the reflux temperature for 2.5 hours, then was allowed to cool to room temperature and stirred at this temperature overnight. The reaction mixture was poured into a two phase mixture of ethyl acetate and aqueous sodium bicarbonate and stirred for 1 hour. The organic layer was separated, dried over anhydrous magnesium sulfate, filtered and evaporated to dryness in vacuo to give a brown oil which was purified by column chromatography on silica gel with ether as the eluant to give 300 mg. (27%) of the desired product; m.p. 60°–64° C.

Anal. Calcd. for C$_{20}$H$_{28}$N$_2$O$_7$: C, 58.81; N, 6.91; N, 6.86; Found: C, 59.02; H, 6.83; N, 7.30

EXAMPLE 22

Pirbuterol Hydrochloride

A solution of 2.0 g., (0.005 mole) of 2-acetoxymethyl-3-acetoxy-6-(1-acetoxy-2-N-acetyl-tert-butylaminoethyl)pyridine in 50 ml. of methanol containing 1 ml. of concentrated hydrochloric acid was heated to reflux for 12 hours. The solvents were removed in vacuo and the residue recrystallized from ethyl acetate to give pirbuterol hydrochloride (900 mg., 58%) m.p. 172°–175° C. (dec.), NMR and tlc in 6:3:1 EtOAz:CH$_3$OH:Et$_2$NH identical to pirbuterol. Prolonged heating results in the formation of 2-hydroxymethyl-3-hydroxy-6-(1-hydroxy-2-aminoethyl)pyridine, m.p. 184°–186° dec.

EXAMPLE 23

3-Benzyloxy-2-methyl-6-[1-acetoxy-2-(N-tert-butylacetamido)ethyl]pyridine N-Oxide 3-Benzyloxy-2-methyl-6-(1-hydroxy-2-tert-butylaminoethyl)pyridine N-oxide is acetylated according to the procedure of Example 19 to yield 3-benzyloxy-2-methyl-6-[1-acetoxy-2-(N-tert-butylaminoacetamido)ethyl]pyridine N-oxide.

EXAMPLE 24

2-Acetoxymethyl-3-benzyloxy-6-[1-acetoxy-2-(N-tert-butylacetamido)ethyl]pyridine 3-Benzyloxy-2-methyl-6-[1-acetoxy-2-(N-tert-butylacetamido)ethyl]pyridine N-oxide is heated in acetic anhydride according to the method of Example 21 to produce 2-acetoxymethyl-3-benzyloxy-6-[1-acetoxy-2-(N-tert-butylacetamido)ethyl]pyridine.

EXAMPLE 25

2-Acetoxymethyl-3-hydroxy-6-[1-acetoxy-2-(N-tert-butylacetamido)ethyl]pyridine

2-Acetoxymethyl-3-benzyloxy-6-[1-acetoxy-2-(N-tert-butylacetamido)ethyl]pyridine is hydrogenolyzed according to the method of Example 10 to produce 2-acetoxymethyl-3-hydroxy-6-[1-acetoxy-2-(N-tert-butylacetamido)ethyl]pyridine.

EXAMPLE 26

Pirbuterol Hydrochloride

2-Acetoxy-3-hydroxy-6-[1-acetoxy-2-(N-tert-butylacetamido)ethyl]pyridine is solvolyzed according to the method of Example 22 to prepare pirbuterol hydrochloride.

EXAMPLE 27

6-[1-Hydroxy-2-(N-tert-butylbenzylamino)ethyl]-2-phenyl-4H-1,3-dioxino[5,4-b]pyridine A solution of 33.0 g. (0.13 mole) 6-(1,2-epoxyethyl)-2-phenyl-4H-1,3-dioxino[5,4-b]pyridine and 22.0 g. (0.135 mole) of N-tert-butylbenzylamine in 200 ml. of methanol was heated to the reflux temperature overnight. Upon cooling there deposited 6-[1-hydroxy-2-(N-tert-butylbenzylamino)ethyl]pyridine which was recrystallized from isopropanol to give 29.4 g. (54%) of the amino alcohol m.p. 126°–130° C.

Anal. Calcd. for $C_{26}H_{30}N_2O_3$: C, 74.61; H, 7.23; N, 6.69; Found: C, 75.04; H, 7.21; N, 7.15.

EXAMPLE 28

2-Hydroxymethyl-3-hydroxy-6-[1-hydroxy-2-(N-tert-butylbenzylamino)ethyl]pyridine Dihydrochloride A solution of 8.40 g. (0.02 mole) 6-[1-hydroxy-2-(N-tert-butylbenzylamino)ethyl]-2-phenyl-4H-1,3-dioxino[5,4-b]pyridine in 75 ml. of methanol containing 10 ml. of concentrated hydrochloric acid was stirred at room temperature for 4 hours, then the solvents were evaporated in vacuo to give a solid. Recrystallization from isopropanol/methanol gave 6.30 g. (74%) of 2-hydroxyethyl-3-hydroxy-6-[1-hydroxy-2-(N-tert-butylbenzylamino)ethyl]pyridine dihydrochloride; m.p. 173°–175° C. (dec.)

Anal. Calcd. for $C_{19}H_{26}N_2O_3 \cdot 2HCl \cdot \frac{1}{2}H_2O$: C, 55.34; H, 7.09; N, 6.80; Found: C, 55.73; H, 7.28; N, 6.90.

EXAMPLE 29

Pirbuterol Hydrochloride

Method A.

In a Parr bottle (250 ml.) there were placed 0.50 g (0.0012 mole) of 6-[1-hydroxy-2-(N-tert-butyl-benzylamino)ethyl]-2-phenyl-4H-1,3-dioxino[5,4-b]pyridine and 500 mg. of 5% palladium on carbon in 20 ml. of methanol. Under a hydrogen pressure of 50 psi the mixture was reacted at room temperature for 2 hours. The catalyst was removed by filtration under a nitrogen atmosphere and the solvent was saturated with dry hydrogen chloride to give pirbuterol hydrochloride 250 mg. (67%); m.p. 174°–176° dec.

Method B

By the same method, 2-hydroxymethyl-3-hydroxy-6-[1-hydroxy-2-(N-tert-butylbenzylamino)ethyl]pyridine is hydrogenolyzed to produce pirbuterol hydrochloride.

We claim:

1. A compound of formula

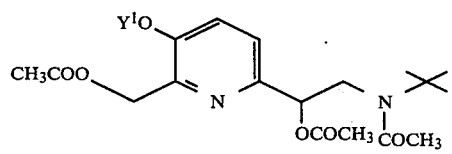

wherein $Y^1$ is benzyl or $COCH_3$.

2. The compound of claim 1 wherein $Y^1$ is benzyl.
3. The compound of claim 1 wherein $Y^1$ is acetyl.

* * * * *